United States Patent [19]

Shioya et al.

[11] Patent Number: 5,040,960
[45] Date of Patent: Aug. 20, 1991

[54] APPARATUS FOR PREPARING ENCAPSULATED BODIES

[75] Inventors: Toshiaki Shioya, Oume; Yasuhiko Shiinoki, Tokyo, Japan

[73] Assignee: Snow Brand Milk Products Co., Ltd., Sapporo, Japan

[21] Appl. No.: 280,939

[22] Filed: Dec. 7, 1988

Related U.S. Application Data

[62] Division of Ser. No. 9,926, Feb. 2, 1987, Pat. No. 4,814,274.

[30] Foreign Application Priority Data

Feb. 13, 1986 [JP] Japan .................. 61-29597

[51] Int. Cl.$^5$ .................. B01J 13/20; A61K 9/66
[52] U.S. Cl. .................. 425/5; 264/4.1; 264/7; 264/14; 425/7; 425/10; 425/68; 425/70
[58] Field of Search .............. 264/7, 12, 14, 4.1–4.7; 425/67–70, 7, 10, 130, 5

[56] References Cited

U.S. PATENT DOCUMENTS

| | | | |
|---|---|---|---|
| 2,402,441 | 6/1946 | Paddle | 425/7 |
| 2,574,357 | 11/1951 | Stammer et al. | 264/7 |
| 3,023,171 | 2/1962 | Smith | 264/14 |
| 4,110,491 | 8/1978 | Secor | 264/4 |
| 4,353,888 | 10/1982 | Sejton | 435/240.22 |
| 4,385,929 | 5/1983 | Ichidate et al. | 264/7 |
| 4,422,985 | 12/1983 | Morishita et al. | 264/14 |
| 4,426,337 | 1/1984 | Suzuki et al. | 264/7 |
| 4,534,917 | 8/1985 | Walz | 425/7 |
| 4,692,284 | 9/1987 | Braden | 425/5 |
| 4,705,755 | 11/1987 | Hasesawa et al. | 435/815 |

FOREIGN PATENT DOCUMENTS

583484  9/1959  Canada .................. 264/4

Primary Examiner—Jay H. Woo
Assistant Examiner—Khanh P. Nguyen
Attorney, Agent, or Firm—Oblon, Spivak, McClelland, Maier & Neustadt

[57] ABSTRACT

An apparatus for the production of encapsulated bodies employing a dropping tank for a fluid to form the cores of the encapsulated bodies and a reaction tank containing a solution capable of forming gel skins upon contact with the core material in communication therewith. Double-walled cylindrical nozzles are arranged in a lower part of the drop tank, the inner and outer walls of the double-walled cylindrical nozzles being coaxial. A pressurized air feed pipe is in communication with an upper part of the dropping tank. The peripheral walls of the reaction tank are in the form of a double-walled cylinder whose upper peripheral portion of its inner wall contains a screen. A liquid feed pipe and a capsule discharge port are provided in communication with the interior of the reaction tank through lower parts of the double-walled cylinder. A liquid discharge port also is provided in communication with an annular spacing of the double-walled cylinder through its outer wall.

The apparatus provides for obtaining a dispersion of encapsulated bodies without their mechanical separation from the liquid in which they are prepared.

3 Claims, 1 Drawing Sheet

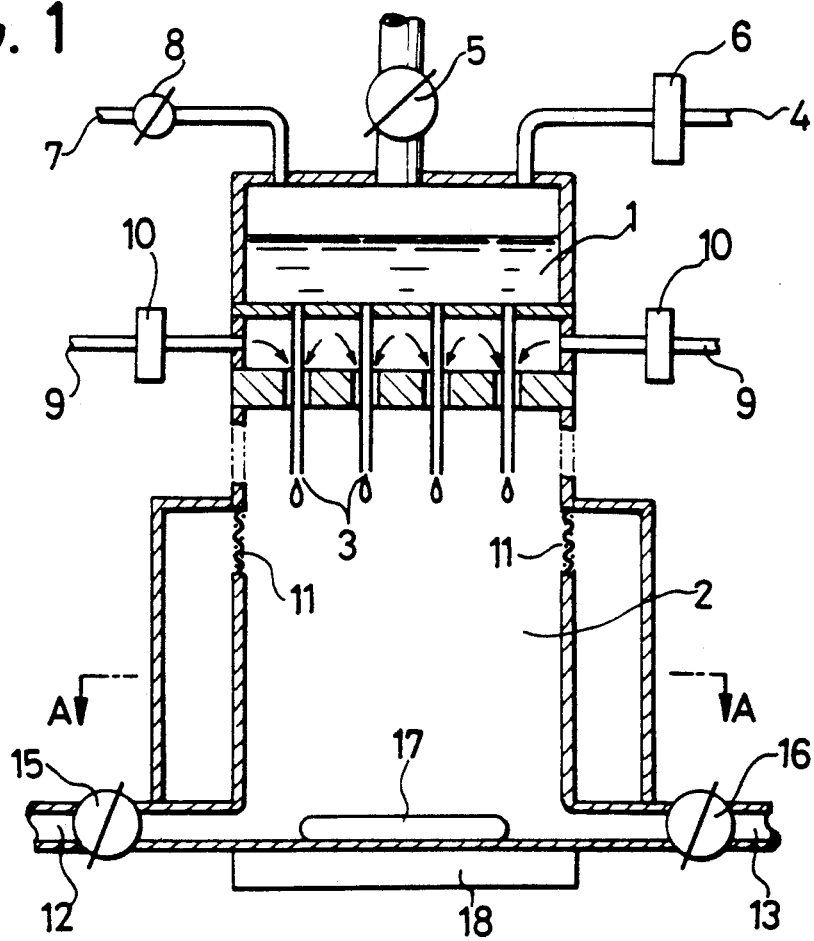
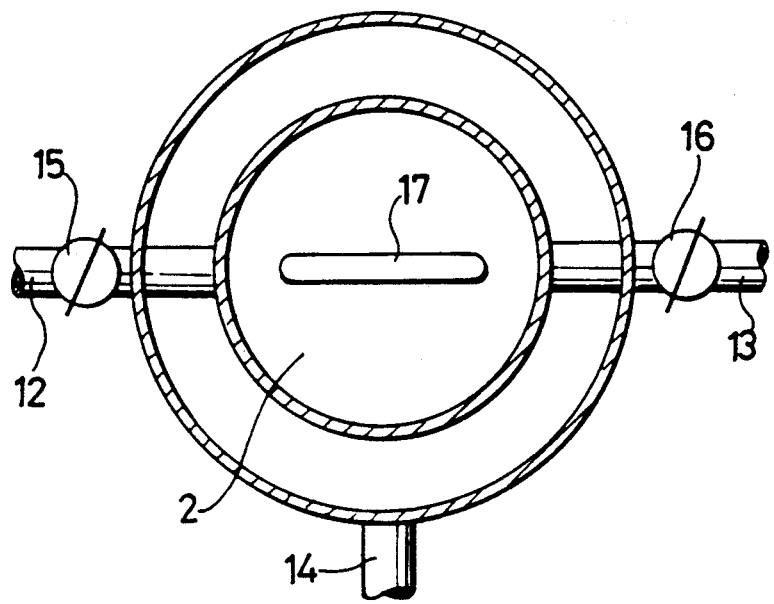

APPARATUS FOR PREPARING ENCAPSULATED BODIES

This is a division of application Ser. No. 07/009,926, filed Feb. 2, 1987, now U.S. Pat. No. 4,814,274.

BACKGROUND OF THE INVENTION

1) Field of the Invention

This invention relates to a process for producing encapsulated bodies by inducing gelation through a liquid-liquid reaction, in which the resulting encapsulated bodies are recovered in a form dispersed in a desired liquid without mechanical separation of the resulting encapsulated bodies from the reaction mixture, and to an apparatus therefor.

2) Description of the Prior Art

In recent years, encapsulation of various liquid materials is practiced in many fields in order to immobilize or otherwise to fix the liquid materials.

For example, there are jelly foods, artificial roe, encapsulated dressing and encapsulated fruit juice in the field of foods.

It is also interested recently in immobilizing microorganisms and enzymes by using capsules or gel particles or granules in the field of so-called biotechnology, especially, in the microencapsulation technique as a method for culturing animal cells.

Incidentally, the culture making use of the aforementioned microencapsulation technique permits protection of cells from mechanical shear forces during the culture. It is also feasible to allow a physiologically active substance, which is to be produced by the cells, to accumulate to a high concentration within the capsules by controlling the permeability of the capsule walls, resulting in the advantages that not only the isolation and recovery of the physiologically active substance but also the separation of the cells and the culture medium are facilitated.

The above-described encapsulation technique is however accompanied by a problem upon its utilization, because damages to the capsules or gel particles formed by the gelation, such as their rupture, are unavoidable due to an application of mechanical separation such as filtration or centrifugation for the separation and recovery of the capsules or gel particles from the reaction mixture. In the case of encapsulation of animal cells or the like, the resultant capsules must be transferred in a sterile state promptly to a culture medium and then to disperse same there. The above-mentioned mechanical separation hence involves the problem that the sterilization procedure becomes very complex.

SUMMARY OF THE INVENTION

This invention has been completed in view of the above-described problems in the production of encapsulated bodies. The present inventors have succeeded in recovering capsules (gel particles), which have been formed through gelation by a liquid-liquid reaction, in a form dispersed in a liquid desired for the utilization of the capsules without damaging the capsules by effecting the separation and recovery of the capsules from the reaction mixture in accordance with a method, in which the liquid portion of the reaction mixture is substituted by the desired liquid, instead of using mechanical separation means.

An object of this invention is therefore to provide a process for recovering, without using mechanical means, encapsulated bodies (e.g., capsules or gel particles), which have been formed by gelation through a liquid-liquid reaction, in a form dispersed in a desired liquid from the reaction mixture in which the encapsulated bodies are dispersed.

In one aspect of this invention, there is thus provided a process for the production of encapsulated bodies by bringing a fluid, which is to form the cores of the encapsulated bodies, and a solution, which has ability to form gel skins upon contact with the fluid, into contact and inducing a gelling reaction therebetween, which comprises introducing a desired liquid, which is suitable for the utilization of the encapsulated bodies, successively into the reaction mixture in which the encapsulated bodies formed by the gelling reaction are dispersed, whereby the liquid portion of the reaction mixture is substituted with the desired liquid and the resultant encapsulated bodies are hence recovered in a form dispersed in the desired liquid.

In another aspect of this invention, there is also provided an apparatus for the production of encapsulated bodies, including a dropping tank for a fluid to be employed to form the cores of the encapsulated bodies and a reaction tank for containing a solution capable of forming gel skins upon contact with the fluid, characterized in that double-walled cylindrical nozzles are arranged in a lower part of the dropping tank, the inner and outer walls of each of the double-walled cylindrical nozzles are coaxial, a pressurized air feed pipe is provided in communication with an upper part of the dropping tank, the peripheral wall of said reaction tank is constructed in the form of a double-walled cylinder, an upper peripheral portion of the inner wall of the double-walled cylinder is formed in the shape of a screen, a liquid feed pipe and a capsule discharge port are provided in communication with the interior of the reaction tank through lower parts of the double-walled cylinder, and a liquid discharge port is formed in communication with the annular spacing, which is defined by the inner and outer walls of the double-walled cylinder, through the outer wall of the double-walled cylinder.

The term "encapsulated bodies" as used herein means not only capsules but also gel particles. The term "desired liquid" will hereinafter be referred to as "dispersing medium" for the sake of simplicity.

The present invention has brought about numerous advantages. According to the present invention, the encapsulated bodies formed by the gelling reaction can be recovered in a form dispersed in a dispersing medium suitable for the utilization of the thus-encapsulated bodies without using mechanical separation means such as filtration or centrifugation. It is therefore possible to obtain the encapsulated bodies in a form conforming with their application purpose without damaging them. In addition, the use of the apparatus of this invention allows to conduct the above-mentioned recovery of the encapsulated bodies and at the same time, to control the size of the encapsulated bodies as desired. Further, the encapsulated culture of animal cells or the like permits their handling in a sterile state.

BRIEF DESCRIPTION OF THE DRAWINGS

FIG. 1 is a side cross-sectional view showing the outline of a production apparatus according to the present invention; and FIG. 2 is a transverse cross-sectional view taken along line A—A in FIG. 1.

DETAILED DESCRIPTION OF THE PREFERRED EMBODIMENTS

As reactant solutions useful for gelation in the production of encapsulated bodies in accordance with this invention, the following combinations may be mentioned by way of example: $Ca^{++}$ containing solution (core liquid)—a solution of sodium alginate or a lowly-methoxylated pectin; and an aqueous solution (core liquid) of a polyanionic polysaccharide such as carboxymethylcellulose or its salt and a solution of chitosan. The latter combination is particularly suitable for the culture of animal cells by the microencapsulation technique, because the gelation can be carried out under mild conditions.

The contact of the reactant solutions in each of the above-mentioned combinations can be effected usually by dropping one of the reactant solutions (for example, a $Ca^{++}$ containing solution, carboxymethylcellulose solution) as a core liquid, into the other reactant solution.

In the present invention, a gelling reaction is induced between both reactant solutions as a result of the dropwise contact of one of the reactant solutions with the other reactant solution so that capsules (or gel particles) are formed and dispersed in the reaction mixture. By substituting the liquid portion of the reaction mixture with a dispersing medium suitable for the utilization of the resultant capsules, the capsules are recovered in a form dispersed in the dispersing medium.

A method, which is useful for the recovery of the resulting capsules in a form dispersed in the dispersing medium in accordance with this invention, will next be described on the basis of an apparatus usable in the practice of the above method.

Reference is first made to FIG. 1. Numeral 1 indicates a dropping tank for a core liquid, whereas numeral 2 designates a reaction tank for storing a liquid which undergoes a gelling reaction with the core liquid upon their mutual contact. The dropping tank 1 has double-walled cylindrical nozzles 3 in a lower part thereof and a pressurized gas feed line 4 in an upper part thereof. The inner and outer walls of each of the nozzles 3 are coaxial.

There are also shown a core solution inlet 5, an air filter 6 for removing bacteria from a pressurized gas to be introduced, a vent pipe 7 for the pressurized gas, and a valve 8 for the vent pipe. Designated at numeral 9 is a feed pipe for another pressurized gas to be introduced into annular spacings between the inner and outer walls of each of the double-walled cylindrical nozzles 3 in order to control the size of droplets of the core solution to be dropped through the nozzles 3. The feed pipe 9 is therefore in communication with the annular spacings. The thus-introduced gas flows out through the annular spacings and then along the imaginary extensions of the inner walls of the nozzles 3, thereby controlling the size of the droplets of the core solution. Numeral 10 indicates an air filter for making the pressurized gas free of bacteria.

On the other hand, the peripheral wall of the reaction tank 2 is formed in the shape of double cylinders. An upper part of the inner peripheral wall of the reaction 2 is formed as a screen-like portion 11. A dispersing medium feed pipe 12 and capsule discharge pipe 13 are provided in lower parts of the reaction tank 2. The dispersing medium feed pipe 12 and capsule discharge pipe 13 are in communication with the interior of the reaction tank 2 through both inner and outer walls of the double-walled cylindrical peripheral wall of the reaction tank 2. Through the outer wall of the peripheral wall, a liquid outlet 14 is also provided in communication with the annular spacing between the inner and outer walls of the peripheral wall.

In the same drawing, numerals 15, 16 indicate valves, numeral 17 a magnetic stirrer provided in the bottom portion of the reaction tank 2, and numeral 18 a rotating electromagnet.

In the present invention, a core solution which is to form the cores of encapsulated bodies is prepared first of all. The core solution is charged through the charging opening 5 into the dropping tank 1. On the other hand, the reaction tank 2 is filled with a solution which undergoes a gelling reaction with the core liquid. When animal cells or the like are encapsulated and cultured, it is necessary to maintain the interior of the apparatus under sterile conditions. Since the dropping tank and reaction tank are provided in continuation in the apparatus, the solution for conducting a gelling reaction is introduced through a dispersing medium feed pipe 12 provided at a lower part of the reaction tank 2.

Pressurized air or the like is then introduced through the pressurized gas feed pipe 4 provided in the upper part of the dropping tank 1 so as to pressurize the core solution, whereby the core solution is dropped into the reactant solution in the reaction tank 2 through the nozzles 3. Another pressurized air or the like is fed through the pressurized gas feed pipe 9 provided through the outer peripheral wall of the reaction tank 2. This pressurized air or the like is then allowed to flow along the imaginary extensions of the inner walls of the nozzles 3, thereby controlling the size of droplets of the core solution to achieve a desired capsule size.

The thus-dropped core solution is thus brought into contact with the reactant solution in the reaction tank 2 to undergo a gelling reaction immediately, so that the droplets of the core solution are converted into capsules or gel particles. Upon conducting the gelling reaction, it is possible to choose stirring conditions, which are most suitable for each one of various encapsulation methods, by using the magnetic stirrer 17 placed in the bottom part of the reaction tank 2 and then to stir the mixture in the reaction tank 2.

Upon completion of the above-described encapsulation, the valve 15 of the dispersing medium feed pipe 12 is opened so as to introduce a dispersing medium, which is suitable for the utilization of the capsules (for example, diluting water, fruit juice, syrup, liquid culture medium), under pressure through the feed pipe 12. Thus, the dispersing medium is introduced successively into the reaction tank 2. Owing to this introduction of the dispersing medium, the liquid level rises in the reaction tank 2. Since the upper part of the inner peripheral wall of the reaction tank 2 is formed as the screen-like portion 11, any extra portion of the liquid is caused to overflow to maintain the predetermined liquid level in the reaction tank 2. The extra portion of the liquid is then allowed to flow down through the spacing between the inner and outer walls of the double-walled cylinder which constitutes the reaction tank 2, whereby the extra portion of the liquid is successively discharged out of the reaction tank 2 through the liquid outlet 14 formed through the outer wall. Here, the capsules dispersed in the reaction mixture are not overflowed owing to the provision of the screen-like portion. Accordingly, the concentration of the reaction mixture in the reaction tank 2 drops exponentially at a rate commensurate with the amount of the dispersing medium introduced under pressure through the feed pipe 12. Upon a lapse of a certain period of time, the liquid portion of the reaction mixture has been substituted with the above-introduced dispersing medium.

In passing, the above-mentioned exponential relation between the concentration of the reaction mixture in the reaction tank and time can be expressed by the following equation.

$$C_t = C_o \exp\left(-\frac{Q}{V} t\right)$$

where
- $C_t$ ... Concentration of the reaction mixture after t hours
- $C_o$ ... Initial concentration of the reaction mixture
- Q ... Flow rate of the introduced dispersing medium
- V ... Volume of the reaction tank
- t ... Introduction time of the dispersing medium At a stage where the reaction mixture in the reaction tank 2 has been substituted practically with the introduced dispersing medium in the manner mentioned above (at this stage, the resultant capsules are either dispersed or suspended in the thus-introduced dispersing medium), the valve 15 of the feed pipe 12 for the dispersing medium is closed and the valve 16 of the capsule discharge pipe 13 is opened so as to discharge and recover the capsules together with the dispersing medium from the reaction tank 2.

When conducting encapsulated culture of animal cells or the like in the present invention, a physiological saline or phosphate-buffered saline (PBS) is introduced in the reaction tank so as to substitute for the liquid portion of the reaction mixture in the reaction tank. The capsules, which contain the animal cells as a core substance, are then recovered in a form dispersed in PBS or the like. The capsule dispersion is thereafter mixed with an equal amount of a culture medium which has been prepared in advance with a concentration twice its usual concentration, followed by culture of the animal cells.

Encapsulated bodies dispersed in a syrup or fruit juice may be obtained by introducing water into a reaction mixture as a dispersing medium at the time of the encapsulation reaction being completed in order to dilute the mixture and then introducing the syrup or fruit juice as the medium thereby recovering capsulated bodies dispersed in the syrup or fruit juice.

The present invention will hereinafter be described more specifically by the following Examples.

EXAMPLE 1

This example illustrates encapsulation of animal cells. A liquid culture medium containing 0.5% of carboxymethylcellulose (CMC), in which a IgG antibody producing hybridoma had been dispersed at a concentration of $2 \times 10^5$ cells/ml, was employed as a core solution. The core solution was charged into the dropping tank 1 of the production apparatus, which is depicted by way of example in FIG. 1, through the core solution inlet 5. The core solution was then dropped under pressure through the nozzles 3, which were provided in the lower part of the dropping tank, formed as double-walled cylinders with the inner and outer walls thereof being coaxial and had an inner diameter of 0.5 mm, into a 0.7% chitosan solution received in the reaction tank 2. The pressurization of the core solution was effected by introducing air under pressure from the pressurized gas feed pipe 4, which was provided in the upper part of the dropping tank, through the air filter into the dropping tank. At the same time, air was also fed from the pressurized gas feed pipe 9, which was connected to the outer walls of the double-walled cylindrical nozzles 3, through the air filter 10 into the annular spacings between the outer and inner walls of the nozzles and was then caused to flow out along the imaginary extensions of the inner walls of the respective nozzles, so that the diameter of the resulting droplets of the core solution was controlled at 2 mm.

The above core solution dropped in the reaction tank 2 was brought into contact with the chitosan solution to induce a gelling reaction. Two to three minutes later, capsules were formed and dispersed in the reaction mixture.

The valve 15 was thereafter opened to successively introduce PBS as a diluent through the dispersing medium feed pipe 12 provided in the lower part of the reaction tank 2, thereby substituting the chitosan solution with PBS.

After the above substitution, the capsules dispersed in PBS were recovered through the capsule discharge pipe provided in the lower part of the reaction tank and then fed to a culture tank, in which the PBS dispersion of the capsules was mixed with an equal amount of a culture medium ["DMEM" (Dulbecco's Modified Eagle's Medium; trade name) and "Ham's F12" (trade name) were used] which had been prepared in advance with a concentration twice its usual concentration, followed by culture of the encapsulated cells.

EXAMPLE 2

This example illustrates encapsulation of a fruit juice.

A core solution was prepared by adding 4 parts by weight of fivefold-concentrated strawberry juice to 100 parts by weight of a sorbitol solution which contained 3% of calcium lactate. Following the procedure of Example 1, the core solution was added dropwise with a droplet size of 6 mm into a 2.5% solution of lowly-methoxylated pectin so that the core solution was encapsulated.

Three minutes after the encapsulating reaction, a sorbitol solution of "Brix45" was introduced successively into the reaction tank in the same manner as in Example 1. The reaction mixture in the reaction tank was substituted with the sorbitol solution and the encapsulated fruit juice was recovered in a form dispersed in the sorbitol solution.

EXAMPLE 3

As a core solution, there was used a yeast dispersion which had been obtained by dispersing yeast at a concentration of 20% (w/v) in a physiological saline containing 4% of κ-carrageenan. Following the procedure of Example 1, the core solution was dropped with a particle size of 4 mm in a 400 mM aqueous solution of potassium chloride, thereby subjecting the droplets of the core solution to a gelling reaction.

Upon a lapse of three minutes from the completion of the gelling reaction, a physiological saline was introduced successively into the reaction tank so as to substitute, with the physiological saline, the liquid portion of the reaction mixture in the reaction tank. The resultant encapsulated yeast was then recovered in a form dispersed in the physiological saline.

What is claimed is:

1. An apparatus for the production of encapsulated bodies, comprising a dropping tank for a fluid to be employed to form the cores of the encapsulated bodies and a reaction tank having a peripheral inner and outer wall for containing a solution forming gel skins upon contact with said fluid in communication therewith, double-walled cylindrical nozzles arranged in a lower part of the dropping tank, the inner and outer walls of each of said double-walled cylindrical nozzles being coaxial, a pressurized air feed pipe in communication with an upper part of said dropping tank, the peripheral walls of said reaction tank comprising a double-walled cylinder whose upper peripheral portion of the inner wall of said double-walled cylinder comprises a screen, a liquid feed pipe and a capsule discharge port in communication with the interior walls of said reaction tank through lower parts of said double-walled cylinder, and a liquid discharge port in communication with an annular spacing defined by the inner and outer walls of said double-walled cylinder through the outer wall of said double-walled cylinder, the interior of said reaction tank being in fluid communication with said annular space through said screen.

2. The apparatus as claimed in claim 1, further comprising a stirring means in a bottom part of the reaction tank for stirring the encapsulated bodies.

3. The apparatus as claimed in claim 1, further comprising a pressurized gas feed pipe in communication with annular spacings of the double-walled cylindrical nozzles, said annular spacings being defined by the inner and outer walls of the respective double-walled cylindrical nozzles.

* * * * *